(12) United States Patent
Trabucco et al.

(10) Patent No.: US 9,416,471 B2
(45) Date of Patent: Aug. 16, 2016

(54) LIGHTWEIGHT QUADRIAXIAL SURGICAL MESH

(71) Applicants: Herniamesh S.R.L., Chivasso (IT); Angela Trabucco, Muttontwon, NY (US)

(72) Inventors: Ermanno E. Trabucco, Muttontown, NY (US); Pier Aldo Crepaldi, Vercelli (IT)

(73) Assignee: HERNIAMESH S.R.L., Chivasso (IT)

( * ) Notice: Subject to any disclaimer, the term of this patent is extended or adjusted under 35 U.S.C. 154(b) by 439 days.

(21) Appl. No.: 13/958,347

(22) Filed: Aug. 2, 2013

(65) Prior Publication Data

US 2013/0317623 A1 Nov. 28, 2013

Related U.S. Application Data

(63) Continuation-in-part of application No. 12/454,308, filed on May 15, 2009, now abandoned.

(30) Foreign Application Priority Data

Jun. 27, 2008 (IT) .............................. MI2008A1186

(51) Int. Cl.
*D04B 21/18* (2006.01)
*D04B 21/12* (2006.01)
*A61F 2/00* (2006.01)
*D04B 21/20* (2006.01)

(52) U.S. Cl.
CPC .............. *D04B 21/12* (2013.01); *A61F 2/0063* (2013.01); *D04B 21/18* (2013.01); *D04B 21/202* (2013.01); *A61F 2/0045* (2013.01); *A61F 2002/0068* (2013.01); *D10B 2509/08* (2013.01)

(58) Field of Classification Search
USPC .................................................... 66/192–196
See application file for complete search history.

(56) References Cited

U.S. PATENT DOCUMENTS

| 998,454 | A | | 7/1911 | Belak |
|---|---|---|---|---|
| 4,518,640 | A | | 5/1985 | Wilkens |
| 5,292,328 | A | | 3/1994 | Hain et al. |
| 5,370,650 | A | | 12/1994 | Tovey et al. |
| 5,569,273 | A | * | 10/1996 | Titone .................... A61F 2/0063 442/1 |
| 6,090,116 | A | | 7/2000 | D'Aversa et al. |
| 6,287,316 | B1 | | 9/2001 | Agarwal et al. |

(Continued)

FOREIGN PATENT DOCUMENTS

| CA | 2450956 A1 | 10/2002 |
|---|---|---|
| EP | 0557964 A1 | 9/1993 |

(Continued)

*Primary Examiner* — Danny Worrell

(74) *Attorney, Agent, or Firm* — Troutman Sanders LLP

(57) ABSTRACT

A method for making a lightweight surgical mesh, having the steps of applying a first set of filaments in a first wale direction and forming a first series of loops at each of a plurality of courses. Applying a second set of filaments in the first wale direction and forming a second series of loops at a first adjacent wale to the first wale direction and a third series of loops at a second adjacent wale opposite the first adjacent wale along the plurality of courses. Further, applying a third set of filaments in the first wale direction so that the second series of loops are formed at the second adjacent wale and the third series of loops are formed at first adjacent wale along the plurality of courses. Additionally, applying a fourth set of filaments that interlace repeatedly with the first set of filaments along the first wale direction.

20 Claims, 17 Drawing Sheets

(56) References Cited

U.S. PATENT DOCUMENTS

| | | | |
|---|---|---|---|
| 6,443,964 B1 * | 9/2002 | Ory | A61F 2/0063 606/151 |
| 6,537,313 B2 * | 3/2003 | Ketharanathan | A61L 27/48 623/1.47 |
| 6,615,618 B2 | 9/2003 | Kost | |
| 6,638,284 B1 * | 10/2003 | Rousseau | A61F 2/0063 606/151 |
| 6,711,919 B1 * | 3/2004 | Arnold | D04B 21/14 66/192 |
| 6,737,371 B1 | 5/2004 | Planck et al. | |
| 6,841,492 B2 | 1/2005 | Bhatnagar et al. | |
| 6,966,918 B1 | 11/2005 | Schuldt-Hempe et al. | |
| 6,971,252 B2 | 12/2005 | Therin et al. | |
| 7,073,538 B2 | 7/2006 | Bhatnagar et al. | |
| 7,614,258 B2 | 11/2009 | Cherok et al. | |
| 8,418,508 B2 * | 4/2013 | Lecuivre | A61F 2/0063 66/170 |
| 8,746,014 B2 * | 6/2014 | Mortarino | A61F 2/0063 66/170 |
| 2002/0049504 A1 | 4/2002 | Barault | |
| 2002/0087174 A1 | 7/2002 | Capello | |
| 2002/0115369 A1 * | 8/2002 | Yokoyama | D04B 21/06 442/308 |
| 2003/0228815 A1 | 12/2003 | Bhatnagar et al. | |
| 2004/0029478 A1 | 2/2004 | Planck et al. | |
| 2004/0172048 A1 | 9/2004 | Browning | |
| 2004/0176658 A1 * | 9/2004 | McMurray | A61F 2/2481 600/37 |
| 2005/0055051 A1 | 3/2005 | Grafton | |
| 2005/0081571 A1 | 4/2005 | Bhatnagar et al. | |
| 2006/0281967 A1 | 12/2006 | Meneghin et al. | |
| 2008/0147198 A1 | 6/2008 | Cherok et al. | |
| 2009/0005867 A1 | 1/2009 | Lefranc et al. | |
| 2009/0326565 A1 | 12/2009 | Trabucco et al. | |
| 2012/0198894 A1 | 8/2012 | Lecuivre et al. | |

FOREIGN PATENT DOCUMENTS

| | | |
|---|---|---|
| EP | 1372526 A1 | 1/2004 |
| EP | 1704832 A2 | 9/2006 |
| FR | 2732582 A1 | 10/1996 |
| GB | 2391177 A | 2/2004 |
| GB | 2406522 A | 4/2005 |
| WO | 02/078568 A1 | 10/2002 |
| WO | 2011/042811 A2 | 4/2011 |
| WO | 2013/026682 A1 | 2/2013 |

* cited by examiner

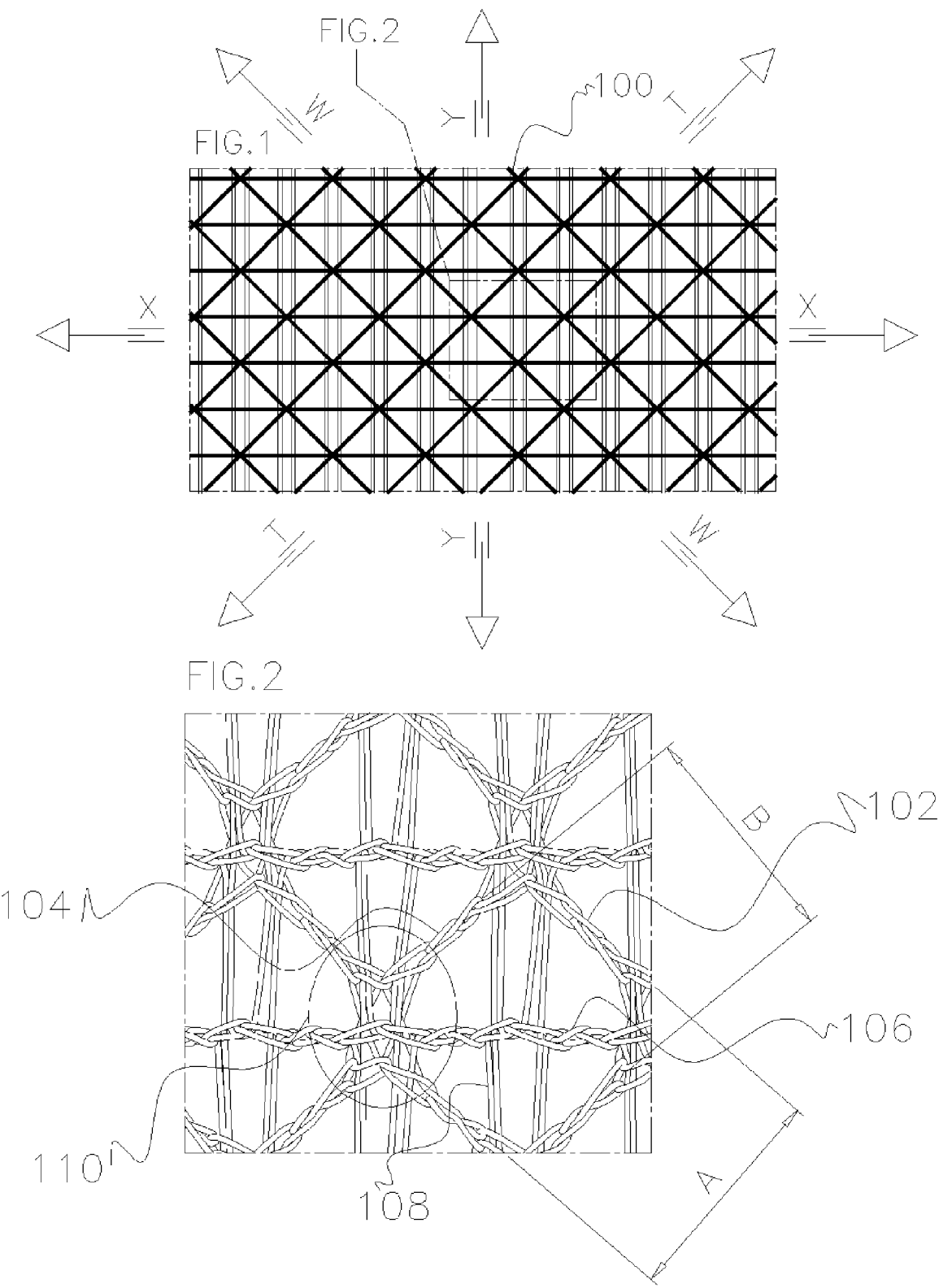

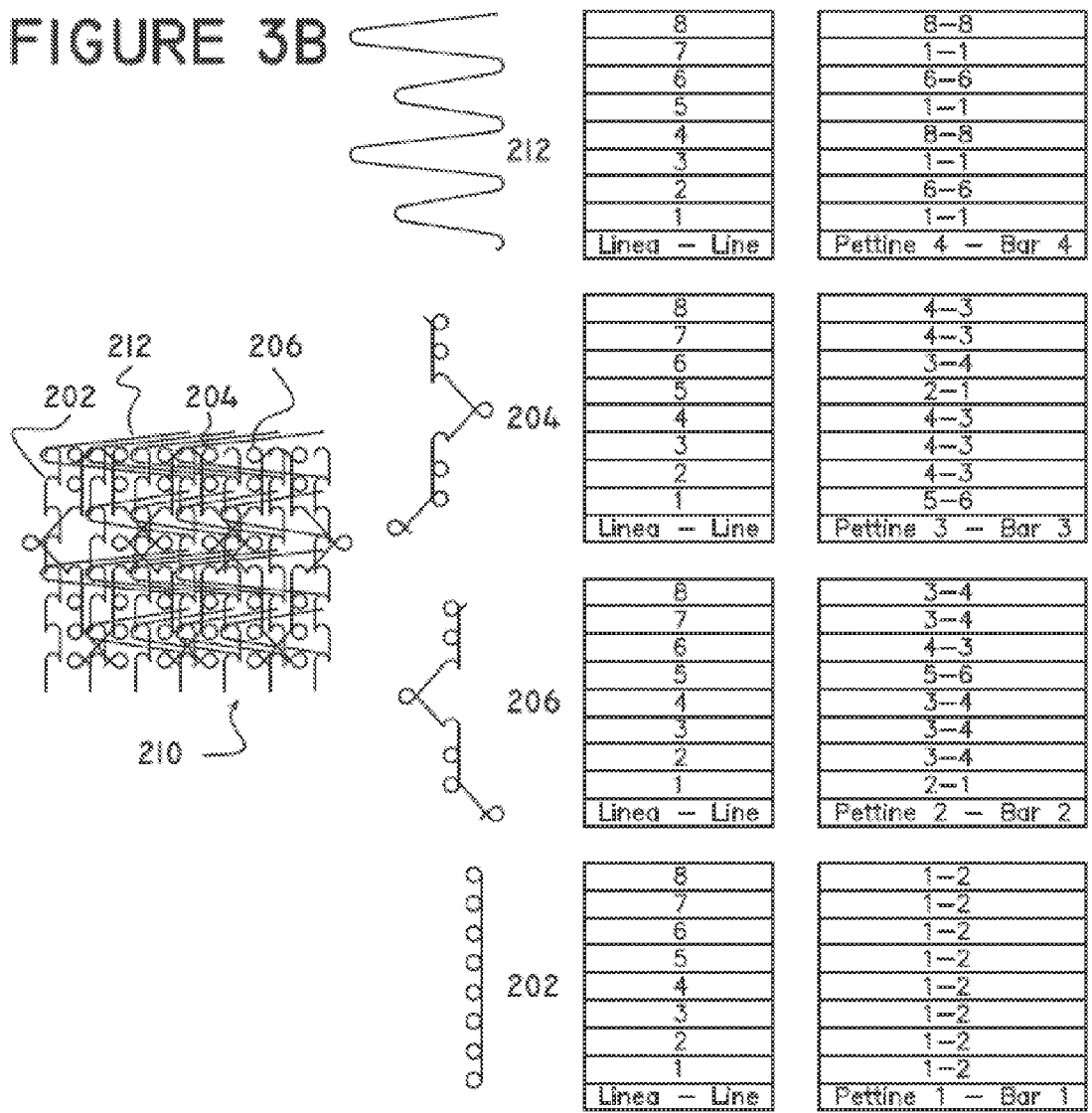
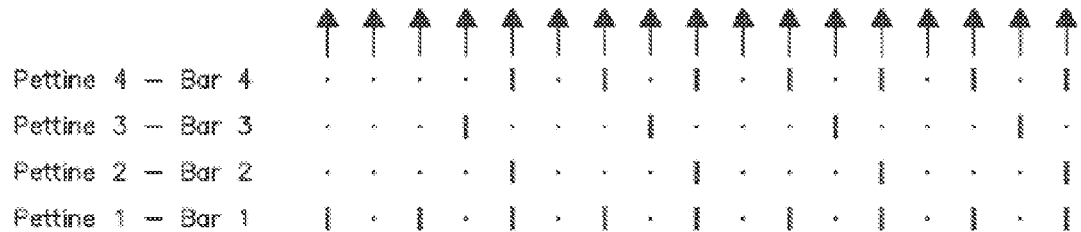
FIGURE 3B

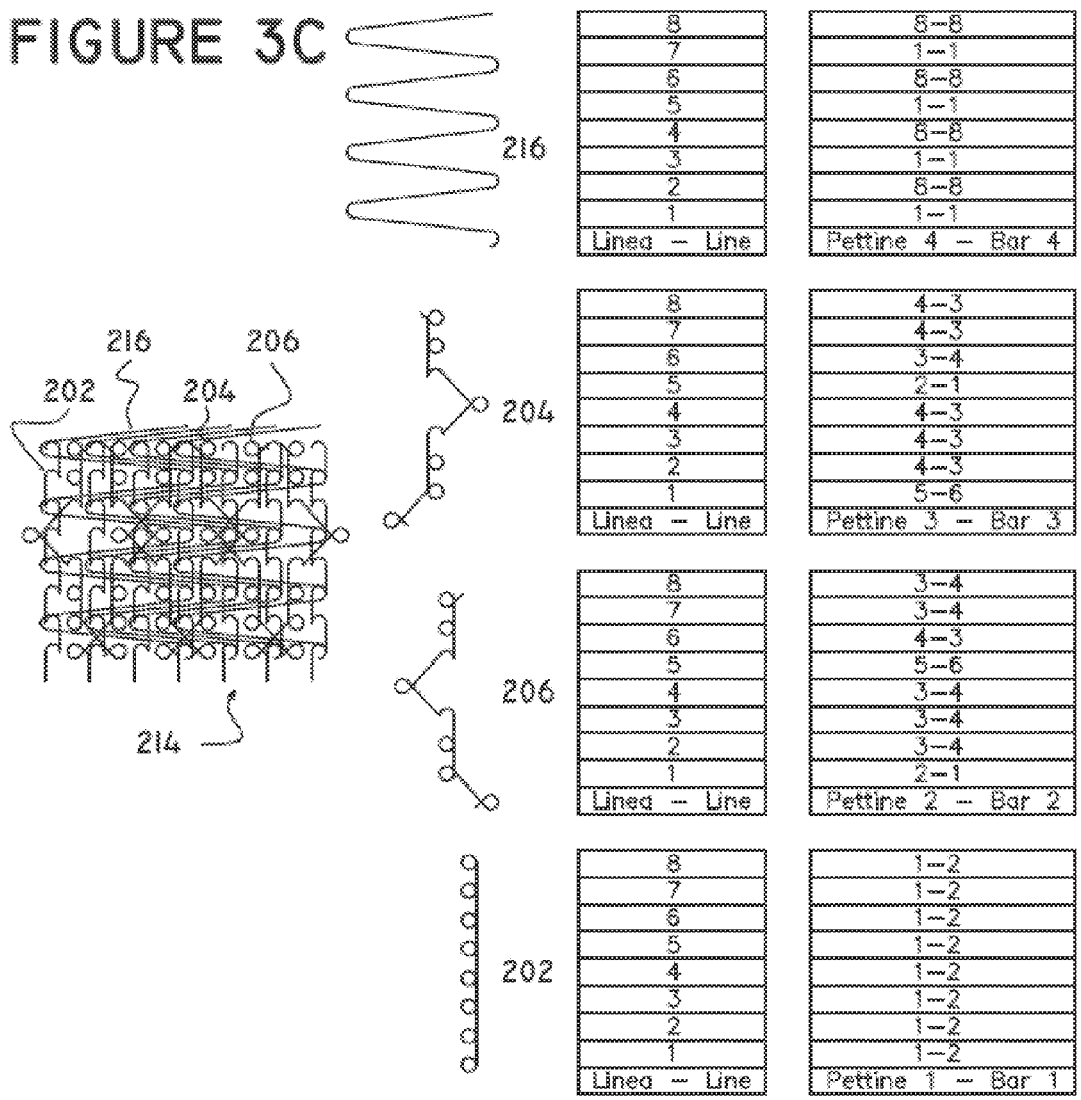
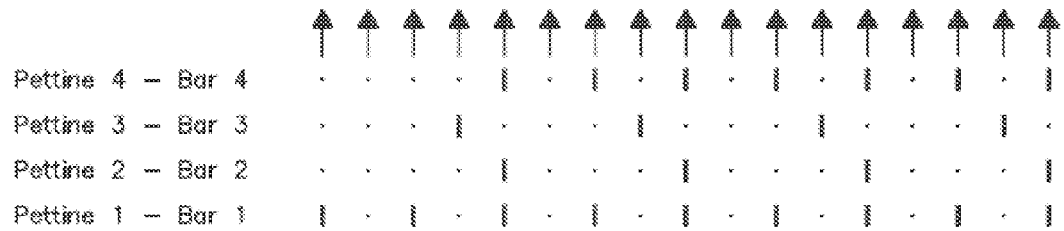
FIGURE 3C

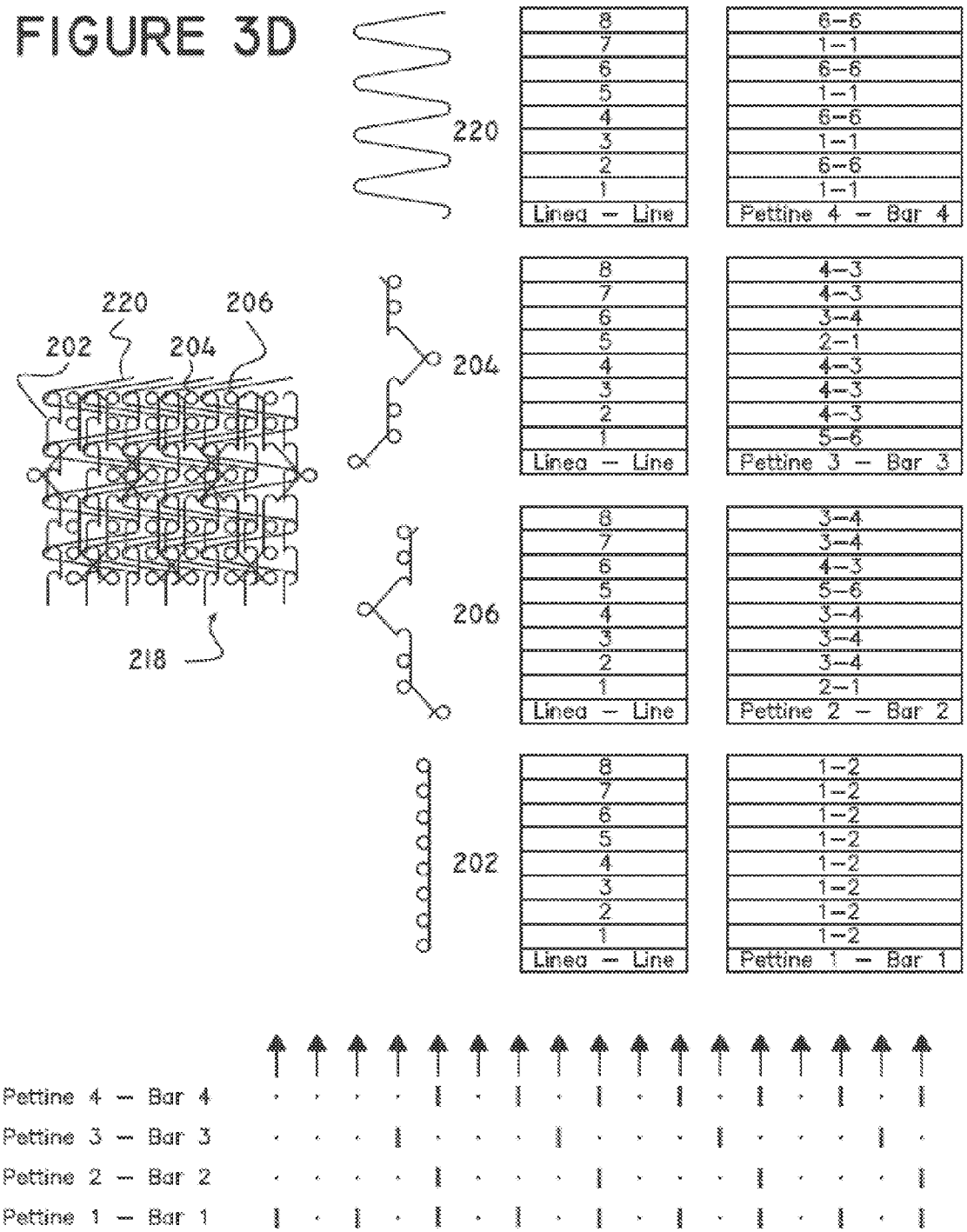

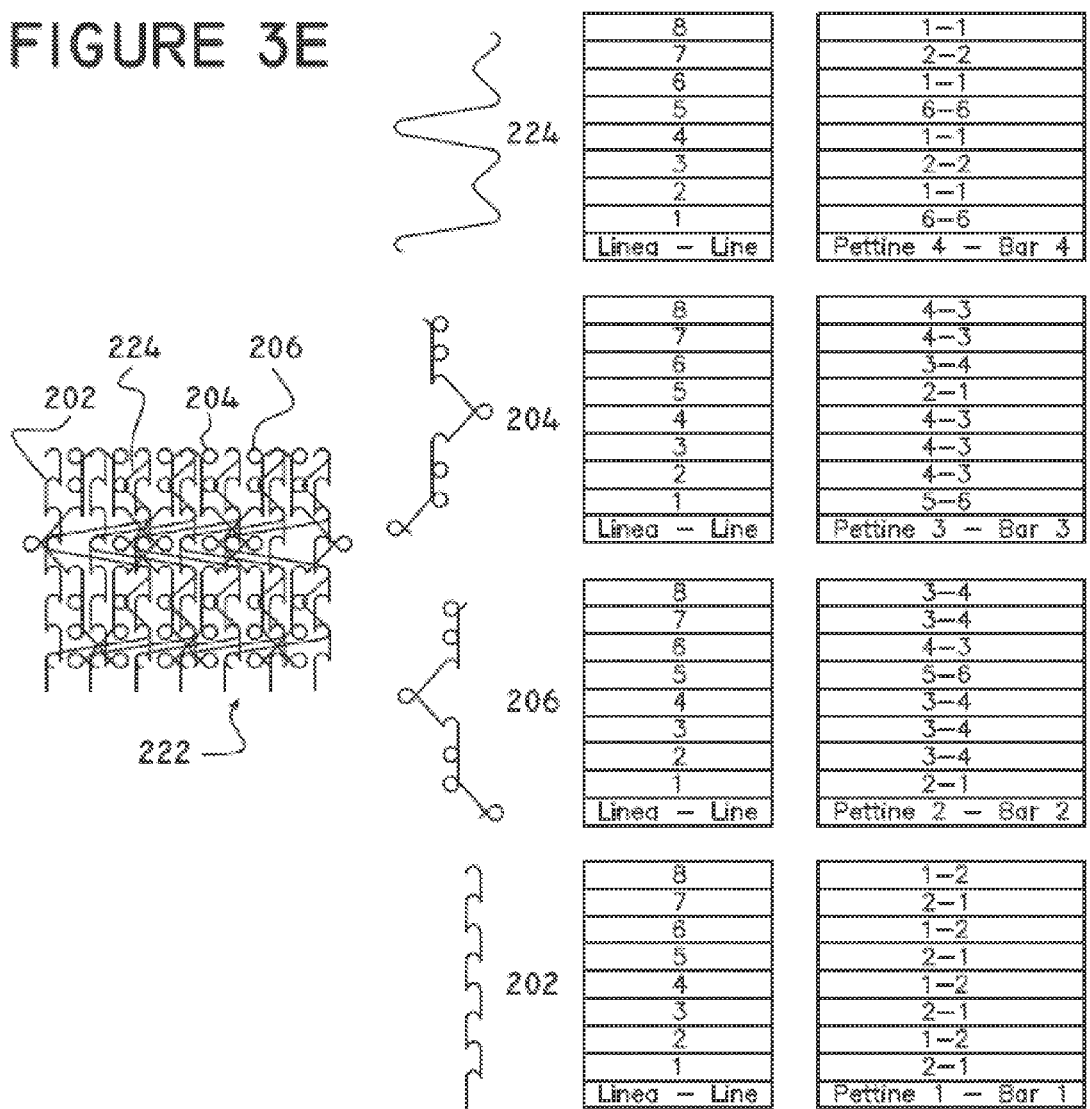
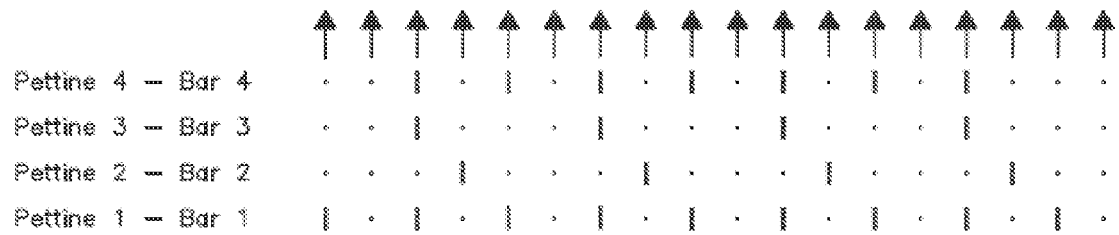
FIGURE 3E

LIGHTWEIGHT QUADRIAXIAL SURGICAL MESH

CROSS-REFERENCE TO RELATED APPLICATIONS

This application is a continuation-in-part of U.S. application Ser. No. 12/454,308 filed May 15, 2009, which further claims priority under 35 U.S.C. §119 to Italian Patent Application No. MI2008A001186, filed Jun. 27, 2008. The entireties of both applications are incorporated herein by reference.

FIELD OF THE INVENTION

This invention relates to a textile material and, in particular, to a surgical mesh of knit construction fabricated using a quadrilateral pattern forming an isotropic mesh.

BACKGROUND

Hernia repairs are among the more common surgical operations which may employ a mesh fabric prosthesis. Such mesh fabric prostheses are also used in other surgical procedures including the repair of anatomical defects of the abdominal wall, diaphragm, and chest wall, correction of defects in the genitourinary system, and repair of traumatically damaged organs such as the spleen, liver or kidney.

The prosthetic surgical meshes can be implanted in either an open surgical procedure or through laparocsopic procedures (i.e. inserting specialized tools into narrow punctures made by the surgeon in the surrounding tissue).

Mesh fabrics as well as knitted and woven fabrics constructed from a variety of synthetic fibers can be used to form the mesh used in surgical repair. It is desirable for a surgical mesh fabric to exhibit certain properties and characteristics. In particular, a mesh suitable for surgical applications should have a tensile strength sufficient to ensure that the mesh does not break or tear after it is implanted in a patient. The mesh should also have a pore size which allows tissue to penetrate or "grow through" the mesh, after the mesh has been implanted into a patient. In addition, the mesh should be constructed so as to maximize flexibility. Increased flexibility helps the mesh mimic the physiological characteristics of the bodily structure it is replacing or reinforcing. An added benefit of increased flexibility facilitates the insertion of the mesh prosthesis into a patient during a surgical operation.

There are competing mesh design concepts one of which is whether to employ a heavyweight mesh with small pores or a lightweight mesh with large pores. The heavyweight meshes are designed to provide the maximum strength for a durable and persistent repair of the hernia. Heavyweight meshes are formed using thick fibers, tend to have smaller pores, and a very high tensile strength. However, the heavyweight mesh may cause increased patient discomfort due to the increase in scar tissue formation.

Lightweight, large pore meshes are better adjusted to the physiological requirements of the body and permit proper tissue integration. These meshes provide the possibility of forming a scar net instead of a stiff scar plate and therefore help to avoid formerly known mesh complications.

However, lightweight meshes have other drawbacks. First, they typically have a lower minimum tensile strength due to the smaller diameter of filament used and the "open" weave. This is also aggravated by the fact that such meshes are formed anisotropic and the differential between the tensile strength in any one of the directions of force can vary significantly. Another drawback to using lightweight meshes is that the anisotropic nature of the mesh has the tendency to cause the mesh to twist or deform when placed under tension, making placement more difficult.

Further, it is desirable for a surgical mesh fabric to have a tensile strength sufficient to ensure that the mesh does not break or tear after implantation into a patient. The minimum tensile strengths for meshes implanted for the augmentation and reinforcement of an existing bodily structure should be at least 16 N/cm. The tensile strength needed for meshes implanted to repair large abdominal hernias can increases to as much 32 N/cm.

These and other objects and advantages of the invention will become more fully apparent from the description and claims, which follow or may be learned by the practice of the invention.

SUMMARY

The invention is a lightweight knitted surgical mesh which includes a first axis, a second axis perpendicular to the first axis, a third axis offset approximately 30° to 60° from the first axis, and a fourth axis perpendicular to the third axis. Further the mesh has a first weave running parallel to the first axis, a second weave running parallel to the second axis, a third weave running parallel to the third axis, and a fourth weave running parallel to the fourth axis. In an embodiment, the third axis is offset 45° from the first axis.

The first weave of the lightweight knitted surgical mesh can include a plurality of parallel filaments, wherein the filaments can be equidistantly or randomly spaced. Alternately, at least two of the first, second, third, and fourth weaves include a plurality of parallel filaments, wherein the filaments for the weaves are equidistantly or randomly spaced. In one embodiment, the filaments for the first weave, the second weave, the third weave, and the fourth weave are all equidistantly spaced to form an isotropic mesh.

The first, second, third, and fourth weaves can include filaments which are at least one of monofilaments and multifilaments. The filaments can have a diameter of 46 dTex and/or a diameter of 60 μm to 180 μm. The filaments can also have a tenacity of 20% to 35% elongation. The lightweight knitted surgical mesh formed of the fibers can have a specific weight of approximately 25 to 200 g/m² and a tensile strength greater than 16 N/cm or 32 N/cm.

The first, second, third, and fourth weaves can include clear filaments and dyed filaments. The spacing between dyed filaments can ½ inch to 2 inches to formed a striped pattern. Further, a region of the mesh can be dyed to increase visibility.

The filaments of the lightweight knitted surgical mesh can be made of polypropylene, polyester, or polyvinylidene fluoride. Further, the filament can be absorbable filaments and/or non-absorbable filaments. Additionally, the filaments can be coated with at least one of expanded poly-tetrafluoroethene/poly-tetrafluoroethylene, Teflon®, and biocompatible synthetic material.

The mesh can also be coated with at least one of a biocompatible synthetic material, titanium, silicone, anti microbial agents, absorbable collagen, non-absorbable collagen, and harvested material.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 1 is a plan view of the surgical mesh of the present invention;

FIG. 2 is a detail view of the mesh of FIG. 1;

FIGS. 3A, 3B, 3C, 3D, and 3E are weaving patterns of separate examples;

DETAILED DESCRIPTION OF THE PREFERRED EMBODIMENT

Figure 3A:
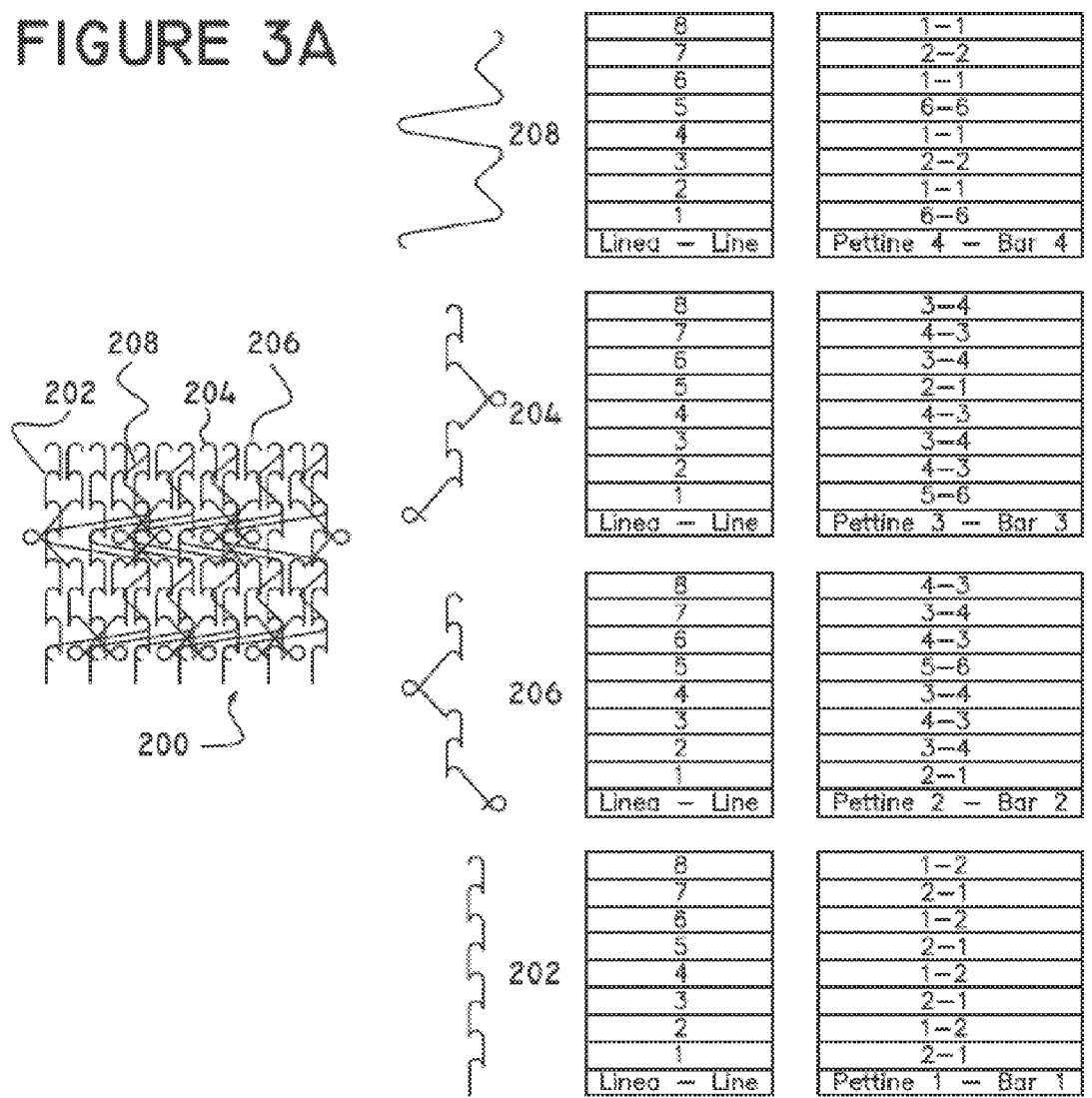

Referring to FIG. 1, a surgical mesh 100 of the present invention is illustrated. Surgical mesh 100 can be surgically implanted in a patient to treat urinary or fecal incontinence resulting from urethral hypermobility or intrinsic sphincter deficiency (ISD). Further, surgical mesh 100 can be implanted to reinforce soft tissue deficiencies. This includes, but is not limited to, pubourethral support and bladder support, urethral and vaginal prolapse repair, pelvic organ prolapse, colon and rectal prolapse repair, incontinence, reconstruction of the pelvic floor, sacral-colposuspension, abdominal wall hernias and chest wall defects. To accomplish the necessary support, mesh 100 can be made into pre-shaped designs, slings, three-dimensional plugs or flat sheets, as needed for each ailment to be corrected.

Surgical mesh 100 is a two bar warp knitted structure. The mesh 100 is subject to numerous forces in tension. Forces are typically applied to the mesh along the X and Y axes X-X; Y-Y. Further, forces can be applied to the mesh along intermediate vectors between the X and Y axes. As illustrated, forces can be applied in T and W axes T-T, W-W. The angle between the X and W axes can be between 30° and 60°, and in one preferred embodiment, 45°. The angle between the Y and T axes can be between 30° and 60°, and in one preferred embodiment, 45°. When the angles between the X and W, and Y and T axes are 45°, the mesh is isotropic. One of ordinary skill in the art can realize that the angle can similarly be measured between the X and T axes and the Y and W axes.

Referring to FIG. 2, mesh 100 is formed from a first weave 102 and a second weave 104. The first and second weaves 102, 104 are long filaments directed along two opposing axes. For example, the weaves 102, 104 can be directed along the X and Y or W and T axes. FIGS. 1 and 2 illustrate the first and second weaves 102, 104 directed along the W and T axes. In one embodiment, the W and T axes are perpendicular and the weaves are spaced equidistant from each other along each axis. As illustrated in FIGS. 1 and 2, the first and second weaves 102, 104 can form a square or diamond shape. In alternate examples, the first weave 102 spacing can differ from the second weave 104 spacing and the two weaves can form rectangles.

In addition to the first and second weaves 102, 104, a third weave 106 and a fourth weave 108 are woven along the remaining two axes. In the illustrated embodiment, third weave 106 is woven along the X-axis and the fourth weave 108 is woven along the Y-axis. In one embodiment, the third and fourth weaves 106, 108 can be perpendicular to each other. Again, the third and fourth weaves 106, 108 can form a square, diamond, or rectangular shapes based on their positioning and the spacing between adjacent weaves on the same axis and the opposing axis.

At or near the points of intersection 110 of the first and second weaves 102, 104 the third and fourth weaves 106, 108 also intersect the first and second weaves 102, 104. Thus, in one embodiment, all four weaves 102, 104, 106, 108 are interwoven with at least one other weave 102, 104, 106, 108 at the intersection points 110. This interweaving adds to the strength of the surgical weave along the four axes X, Y, T, W and provides the mesh 100 with an isotropic pattern, when the weaves are properly spaced.

FIGS. 3A-3E illustrate different weaving examples that can be employed to form mesh 100. The pattern chain for the weaving pattern 200 is as illustrated. FIG. 3A shows weaving pattern 200 which represents a surgical mesh that can be manufactured on a single needle bed thanks to the use of four bars whose movements are represented in the same figure. The first yarn 202 creates wale structure, conferring stability to the fabric in the vertical direction. The two yarns of the wale, 204 and 206, interlace with the first yarn 202 creating a structure which is elastic and uniform. The last yarn 208 is the course that interlacing repeatedly to yarn 202 adds stability to the fabric in the transversal direction.

FIG. 3B illustrates a second weaving pattern 210. First, second, and third filaments 202, 204, 206 perform the same structural purposes as previously discussed. However, the first, second, and third filaments 202, 204, 206 have slightly different bar patterns and the fifth filament 212 (the fourth for pattern 210, but distinguished from fourth filament 208) is woven in a separate pattern. The pattern chain for the weaving pattern 210 is as illustrated.

FIG. 3C is a third weaving pattern 214. First, second, and third filaments 202, 204, 206 remain the same as previously discussed in FIG. 3B, however, sixth filament 216 (the fourth for pattern 214, but distinguished from fourth filament 208 and fifth filament 212) is woven in a separate pattern. The pattern chain for the weaving pattern 214 is as illustrated.

FIG. 3D is a fourth weaving pattern 218. First, second, and third filaments 202, 204, 206 remain the same as previously discussed in FIG. 3B, however, seventh filament 220 (the fourth for pattern 218, but distinguished from fourth filament 208, fifth filament 212, and sixth filament 216) is woven in a separate pattern. The pattern chain for the weaving pattern 218 is as illustrated.

FIG. 3E is a fifth weaving pattern 222. First filament 202 is weaved similar to first filament 202 in FIG. 3A while the second and third filaments 204, 206 remain the same as previously discussed in FIG. 3B. However, eighth filament 224 (the fourth for pattern 218, but distinguished from fourth filament 208, fifth filament 212, sixth filament 216, and seventh filament 220) is woven in a separate pattern. The pattern chain for the weaving pattern 222 is as illustrated.

Relating the filaments (first through eighth, 202, 204, 206, 208, 212, 216, 220, 224) to the weaves (first through fourth, 102, 104, 106, 108), the first filament 202 forms the third weave 106. The second and third filaments 204, 206 form the first and second weaves 102, 104 and the fourth filament 208, fifth filament 212, sixth filament 216, seventh filament 220, and eighth filament 228 form the fourth weave 108.

Each filament (first through eighth, 202, 204, 206, 208, 212, 216, 220, 224) can be a monofilament comprising a single strand of yarn or a multi-filament yarn. The diameter of the filaments can be between 60 μm and 180 μm. The diameter of the individual filaments (first through eighth, 202, 204, 206, 208, 212, 216, 220, 224) can be the same or different, depending on the use. In an embodiment, the filaments can be made from polypropylene (PP), polyester, or polyvinylidene fluoride (PVDF). The individual filaments can be coated in expanded poly-tetrafluoroethene/poly-tetrafluoroethylene (ePTFE), Teflon® and/or other biocompatible synthetic material. Further, certain sections of the filaments can be coated on one or both sides depending on use.

In another embodiment, the filaments can be an interwoven combination of PP and an absorbable polymer filament such as polyglactin (PGLA), poly-1-lactide acid (PLLA), poly-dioxanone/poly-p-dioxanone (PDO or PDS), polycaprolacton or polyglecaprone. This embodiment reduces the amount of PP that remains in the body. In this regard, one or more of the filaments (first through eighth, 202, 204, 206, 208, 212, 216, 220, 224) can be PP while the remaining filaments are an absorbable polymer. Alternately, the PP mesh implant can be coated with an absorbable or non-absorbable polymer (PLLA, PGLA) on one or both sides or a portion of the implant mesh. Also, the PP mesh implant can be coated with titanium, silicone, or anti microbial agents.

In a further embodiment, the PP mesh implant can be coated, on one side or both, in the entirety or on only a portion, with a natural material such as collagen. The collagen can be equine, porcine or bovine and either is absorbable or non-absorbable. In an alternate embodiment, the PP mesh can be layered, either in whole or a portion, with harvested material (i.e. human cadaver tissue, or suitable non-human tissue). The use of collagen or harvested material prevents erosion of the tissue with which the mesh is in contact.

The coating of the filaments and/ or mesh serves different purposes. The implantation of a mesh into the human body is best between two or more muscles. Surgical mesh implanted in contact with organs or tissue can form adhesions or erosions. Certain coatings above reduce the likelihood that the mesh will form adhesions or erode the organ or tissue it contacts. Part of the erosion problem is that when the mesh is trimmed to size, the cut edges remain rough and can cause tissue/organ damage over time. Also the texture of PP mesh itself causes a foreign body reaction so when it is in contact with organs or in a sub-cutaneous position the rates of adhesions and/or erosions are greater. However, coating too much of the surface of the mesh can reduce the mesh's ability to be integrated into the surrounding tissue, it is the foreign body reaction (FBR) of the PP mesh which causes the in growth of fibrous tissue into prosthetic material and the actual mesh fixation.

The use of absorbable coatings and filaments serves the purpose to increase the structural stability of the mesh, without adding to the total load of PP in the patient. The additional absorbable fibers/coatings stiffen the mesh to make it easier for the surgeon to implant. The absorbency of the material is such that within a set period of time after the mesh in implanted (i.e. days to months) the material is absorbed into the body. This now gives the mesh a desired flexibility which can lead to reduced erosion and added comfort to the patient because the reduced FBR which results in a less dense fibrous tissue.

Regardless of the filament material and/or coating, one or more of the filaments (first through eighth, 202, 204, 206, 208, 212, 216, 220, 224) can be colored. The colored filaments can be spaced apart to form stripes to improve visibility of the mesh 100 after it has become wet with body fluids. The spacing of the colored filament can be ½ inch to 2 inches apart. Additionally, a portion of the mesh can be colored to aid in positioning the center of the mesh where it is necessary. For example, for placement of the mesh under the urethra, the central portion (2-4 cm$^2$) of the mesh can be colored. The coloring can be an FDA approved color for PP and in one embodiment, the filaments can be colored blue. In another embodiment, certain materials and finishes of the filaments can lead to a greater light reflectance. Filaments of higher reflectivity can be interwoven to form the same stripe or center identification pattern as coloring.

As discussed above, the diameter of the filaments can be between 60 μm and 180 μm. In one embodiment, the filament is 80 μm±10%. This filament diameter corresponds to approximately 46 dTex. The filament can be spun to have a tenacity of approximately 4.5 cN/dTex. Further, the filament can have an elongation at break once stretched. In one embodiment, the tenacity can be from 20% to 35% elongation. The woven mesh can vary in thickness from 0.25 to 0.80 millimeters and in one embodiment is 0.32 mm±10%. The mesh can have customarily weights approximately 30 g/m$^2$±8%. The specific weight of the mesh can vary between approximately 25 and 200 g/m$^2$. The tensile strength of the mesh is at least 16 N/cm and can further be 32 N/cm. In one embodiment, the tensile strength is greater than 20 N/cm while still retaining an elasticity of 20%-35%.

Figure 4:
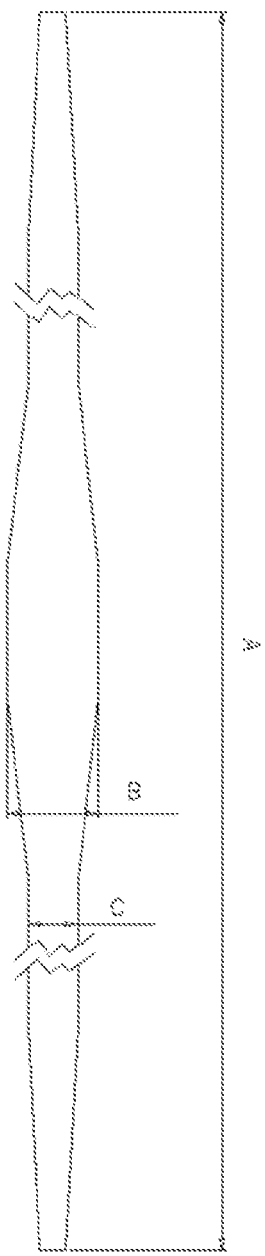
FIG. 4 is a plan view of a sling for urinary incontinence (male or female) made of the mesh of the present invention.
Figure 5:
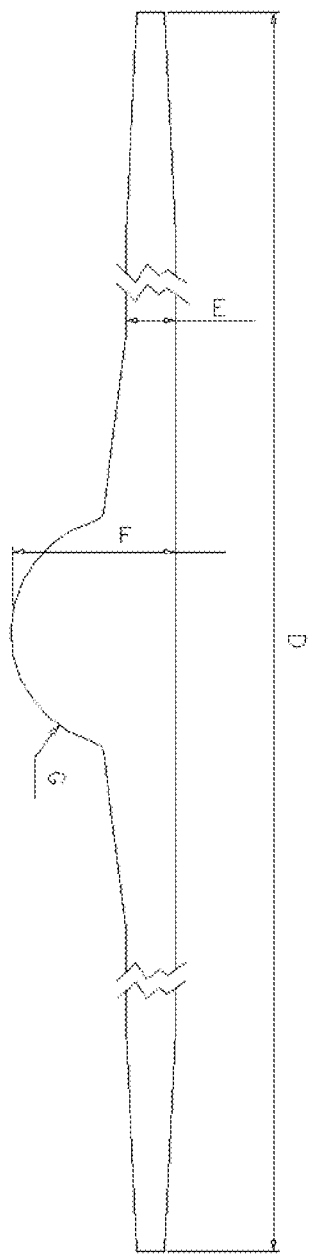
FIG. 5 is a plan view of a sling for urinary incontinence in females associated with a cystocele made of the mesh of the present invention.
Figure 6:
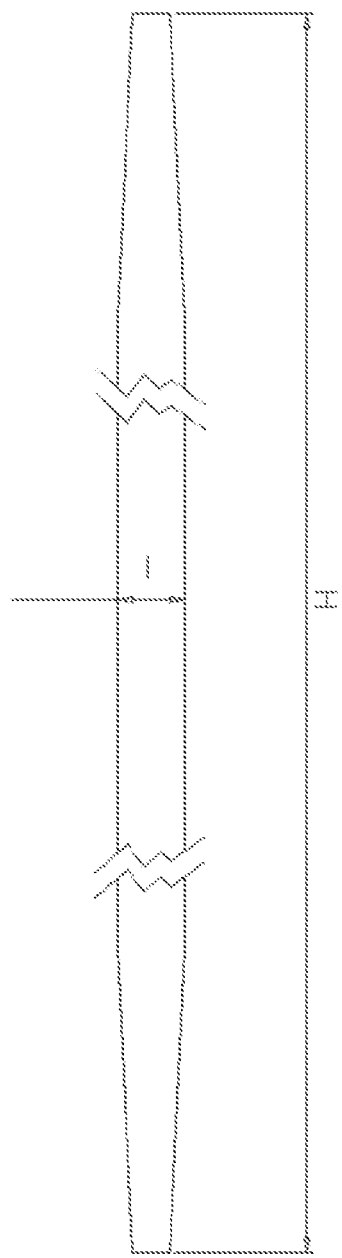
FIG. 6 is a plan view of a sling for urinary incontinence in females and for vaginal vault support made of the mesh of the present invention.
Figure 7:
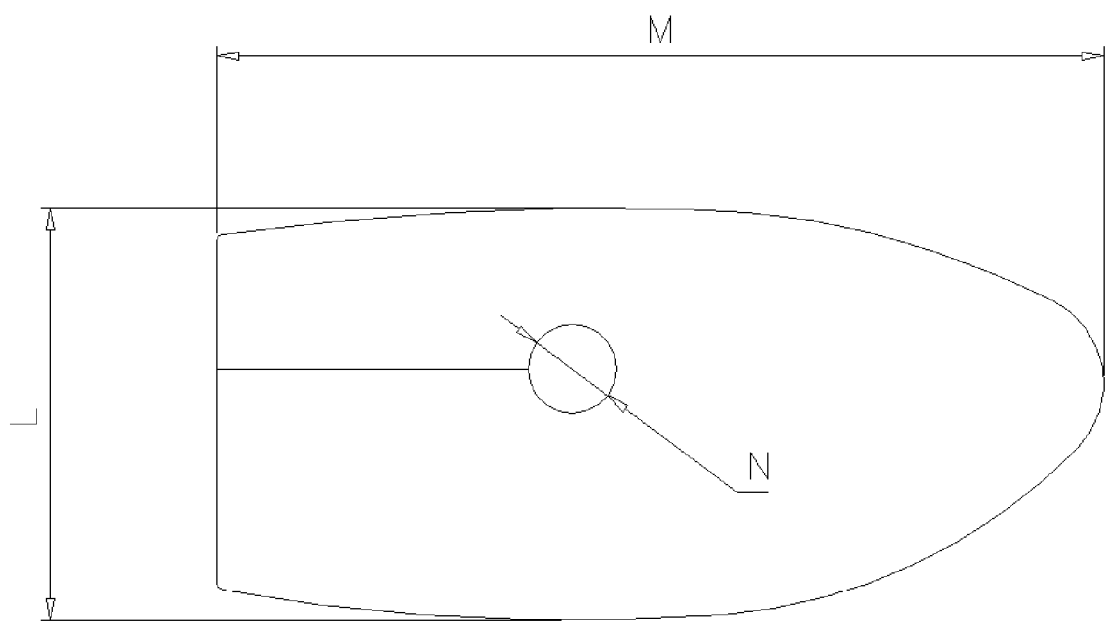
FIG. 7 is a plan view of an inguinal hernia repair in men made of the mesh of the present invention.
Figure 8:
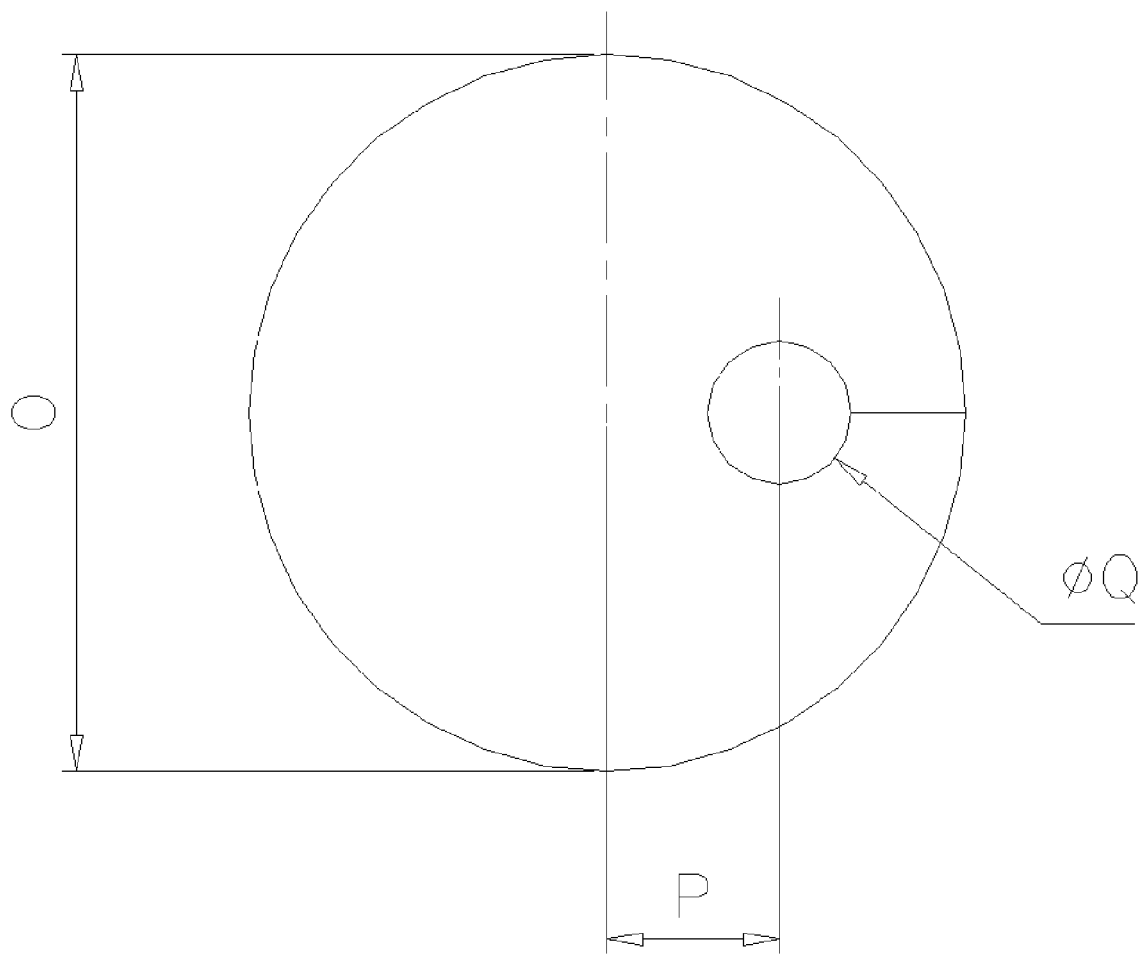
FIG. 8 is a plan view of another inguinal hernia repair in men made of the mesh of the present invention.
Figure 9:
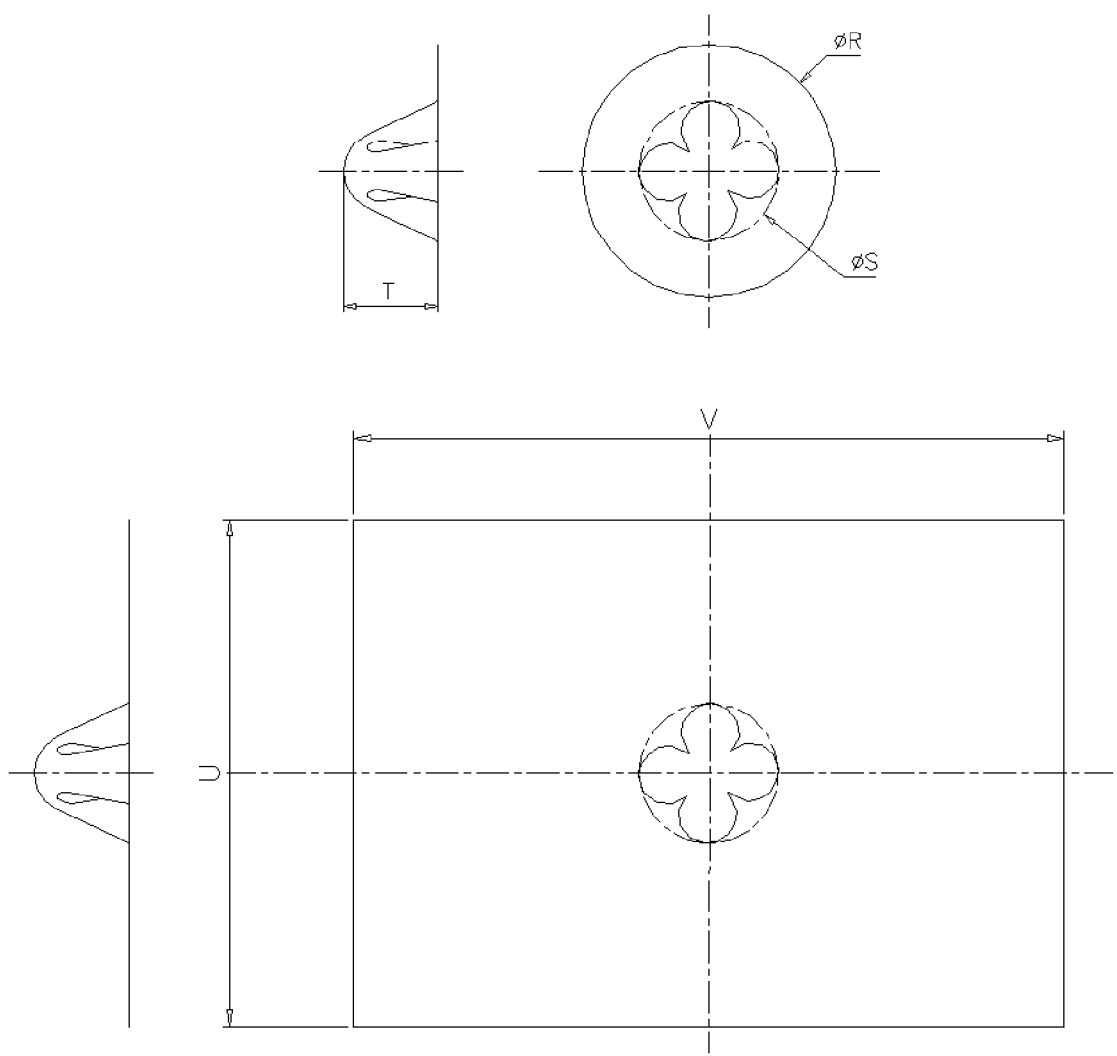
FIG. 9 is a plan view of an abdominal wall hernias made of the mesh of the present invention.
Figure 10:
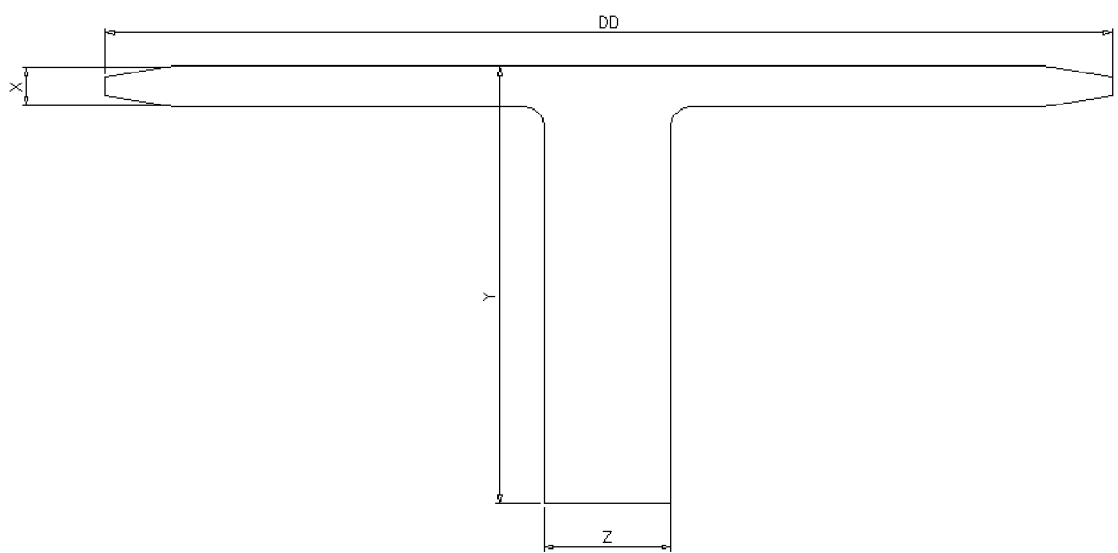
FIG. 10 is a plan view of a sling for pelvic floor repair made of the mesh of the present invention.
Figure 11:
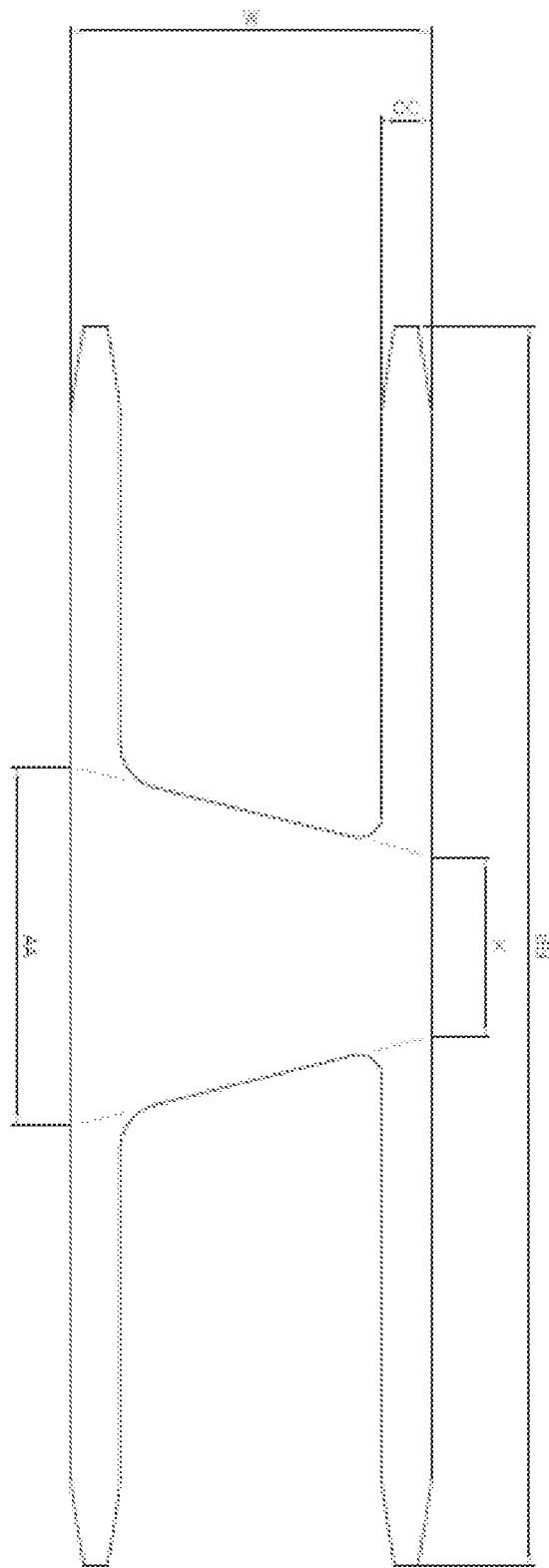
FIG. 11 is a plan view of another sling for pelvic floor repair made of the mesh of the present invention.
Figure 12:
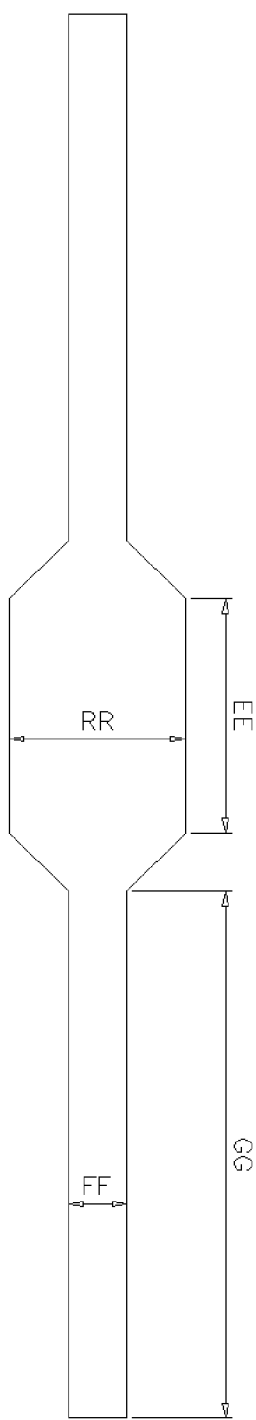
FIG. 12 is a plan view of a further sling for urinary incontinence and pelvic floor repair made of the mesh of the present invention.
Figure 13:
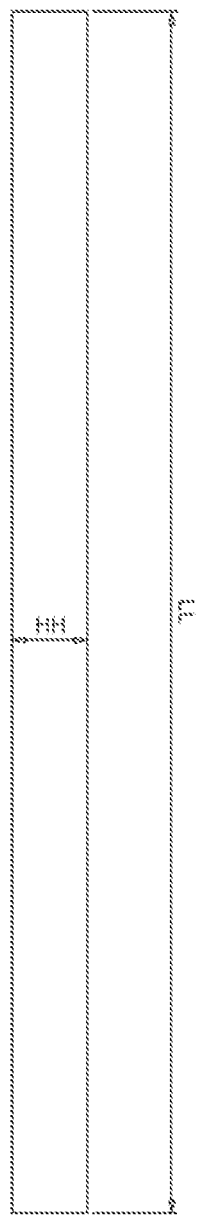
FIG. 13 is a plan view of a sling for urinary incontinence made of the mesh of the present invention.
Figure 14:
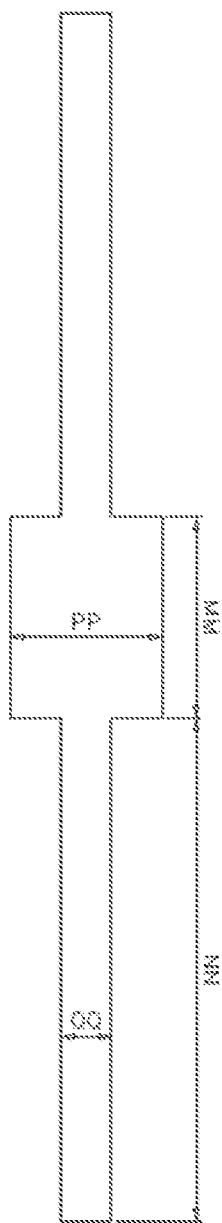
FIG. 14 is a plan view of another sling for urinary incontinence made of the mesh of the present invention.

FIGS. 4-14 illustrate different examples of surgical slings made of the mesh of the present invention. The dimensions noted in the Figures are below in Table 1. FIG. 4 illustrates a sling for urinary incontinence (male or female). FIG. 5 illustrates a sling for urinary incontinence in females associated with a cystocele. FIG. 6 illustrates a sling for urinary incontinence in females and for vaginal vault support. FIG. 7 illustrates an inguinal hernia repair in men and the same configuration without the hole is for inguinal repair in women. FIG. 8 illustrates another inguinal hernia repair in men. FIG. 9 illustrates an abdominal wall hernia repair. FIG. 10 illustrates a device for pelvic floor repair. FIG. 11 illustrates another device for pelvic floor repair. FIG. 12 illustrates a further sling for urinary incontinence and pelvic floor repair. FIG. 13 illustrates a sling for urinary incontinence. FIG. 14 illustrates another sling for urinary incontinence.

TABLE 1

| FIG. | Dimension | Length (mm) |
| --- | --- | --- |
| 4 | A | 20 to 50 |
| 4 | B | 12 to 30 |
| 4 | C | 9 to 20 |
| 5 | D | 20 to 50 |
| 5 | E | 9 to 20 |
| 5 | F | 30 to 40 |
| 5 | G | 20 to 30 |
| 6 | H | 20 to 50 |
| 6 | I | 9 to 20 |
| 7 | L | 40 to 65 |

TABLE 1-continued

| FIG. | Dimension | Length (mm) |
|---|---|---|
| 7 | M | 90 to 140 |
| 7 | N | 9 to 13 |
| 8 | O | 40 to 60 |
| 8 | P | 0 to 15 |
| 8 | Q | 9 to 13 |
| 9 | R | 25 to 75 |
| 9 | S | 12 to 45 |
| 9 | T | 9 to 30 |
| 9 | U | 30 to 140 |
| 9 | V | 30 to 140 |
| 10 | X | 9 to 20 |
| 10 | Y | 100 to 140 |
| 10 | Z | 30 to 60 |
| 10 | DD | 20 to 50 |
| 11 | K | 30 to 50 |
| 11 | W | 50 to 90 |
| 11 | AA | 50 to 90 |
| 11 | BB | 20 to 50 |
| 11 | CC | 9 to 20 |
| 12 | RR | 20 to 80 |
| 12 | EE | 40 to 80 |
| 12 | FF | 6 to 20 |
| 12 | GG | 130 to 210 |
| 13 | HH | 10 to 40 |
| 13 | LL | 200 to 450 |
| 14 | MM | 20 to 80 |
| 14 | NN | 150 to 300 |
| 14 | PP | 20 to 80 |
| 14 | QQ | 10 to 20 |

While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A method for making a lightweight knitted surgical mesh, comprising the steps of:
    applying a first set of filaments in a first wale direction on a single needle bed machine, each of the first set of filaments forming a first series of loops at each of a plurality of courses for the surgical mesh;
    applying a second set of filaments in the first wale direction on the single needle bed machine, each of the second set of filaments forming a second series of loops at a first adjacent wale to the first wale direction and a third series of loops at a second adjacent wale opposite the first adjacent wale along the plurality of courses;
    applying a third set of filaments in the first wale direction on the single needle bed machine, wherein the second series of loops are formed at the second adjacent wale and the third series of loops are formed at first adjacent wale along the plurality of courses; and
    applying a fourth set of filaments that interlace repeatedly with the first set of filaments along the first wale direction.

2. The method of claim 1, wherein:
    the first set of filaments confer stability to the surgical mesh in the first wale direction;
    the second and third sets filaments interlace with the first set of filaments to form an elastic and uniform structure to the surgical mesh; and
    the fourth set of filaments adds stability to the surgical mesh in the transversal direction.

3. The method of claim 1, wherein the first, second and third series of loops are at least one of full loops or partial loops.

4. The method of claim 1, wherein the first, second, third, and fourth set of filaments comprise at least one of monofilaments and multi-filaments.

5. The method of claim 1, wherein the first, second, third, and fourth sets of filaments comprise a diameter of 46 dTex.

6. The method of claim 1, wherein the first, second, third, and fourth sets of filaments comprise a diameter of 60 μm to 180 μm.

7. The method of claim 1, wherein the first, second, third, and fourth sets of filaments comprise a tenacity of 20% to 35% elongation.

8. The method of claim 1, wherein the surgical mesh comprises a specific weight of approximately 25 to 200 g/m$^2$.

9. The method of claim 1, wherein the first, second, third, and fourth sets of filaments comprise at least one of clear filaments and dyed filaments.

10. The method of claim 9, further comprising the step of spacing the dyed filaments ½ inch to 2 inches apart.

11. The method of claim 1, wherein the first, second, third, and fourth sets of filaments comprise one of polypropylene, polyester, or polyvinylidene fluoride.

12. The method of claim 1, wherein the first, second, third, and fourth sets of filaments comprise a coating comprising at least one expanded poly-tetrafluoroethene/poly-tetrafluoroethylene, Teflon®, and biocompatible synthetic material.

13. The lightweight knitted surgical mesh of claim 6, wherein the mesh comprises a coating comprising at least one of biocompatible synthetic material, titanium, silicone, anti microbial agents, absorbable collagen, non-absorbable collagen, and harvested material.

14. The method of claim 1, wherein the first, second, third, and fourth sets of filaments comprise at least one of absorbable filaments and non-absorbable filaments.

15. The method of claim 1, further comprising the steps of:
    forming a first weave, a second, weave, a third weave, and a fourth weave from the first, second, third, and fourth sets of filaments
    applying the first weave parallel along a first axis;
    applying the second weave parallel along a second axis perpendicular to the first axis;
    applying the third weave parallel along a third axis offset approximately 30° to 60° from the first axis; and
    applying the fourth weave parallel along a fourth axis perpendicular to the third axis.

16. The method of claim 1, further comprising the step of offsetting the third axis 45° from the first axis.

17. The method of claim 1, further comprising the step of equidistantly spacing the filaments of the first weave.

18. The method of claim 1, further comprising the step of equidistantly spacing the filaments of at least two of the first weave, the second weave, the third weave, and the fourth weave.

19. The method of claim 1, further comprising the step of equidistantly spacing the first weave, the second weave, the third weave, and the fourth weave, forming an isotropic mesh.

20. The method of claim 1, wherein the surgical mesh comprises a tensile strength greater than 16 N/cm.

* * * * *